(12) United States Patent
Koto

(10) Patent No.: US 8,617,970 B2
(45) Date of Patent: Dec. 31, 2013

(54) METHOD OF MANUFACTURING SEMICONDUCTOR DEVICE

(75) Inventor: Makoto Koto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/582,134

(22) PCT Filed: Feb. 23, 2011

(86) PCT No.: PCT/JP2011/054673
§ 371 (c)(1),
(2), (4) Date: Aug. 31, 2012

(87) PCT Pub. No.: WO2011/111574
PCT Pub. Date: Sep. 15, 2011

(65) Prior Publication Data
US 2012/0329253 A1 Dec. 27, 2012

(30) Foreign Application Priority Data
Mar. 11, 2010 (JP) .................................. 2010-054718

(51) Int. Cl.
*H01L 21/20* (2006.01)
(52) U.S. Cl.
USPC ........... 438/478; 438/503; 438/584; 438/614; 438/618; 438/674; 257/211; 257/301; 257/315; 257/330; 257/E21.101

(58) Field of Classification Search
None
See application file for complete search history.

(56) References Cited

U.S. PATENT DOCUMENTS

2008/0284544 A1* 11/2008 Hashimura .................... 333/197
2009/0212437 A1    8/2009 Kumagai

FOREIGN PATENT DOCUMENTS

| JP | 2005-159332 A | 6/2005 |
| JP | 2007-220742 A | 8/2007 |
| JP | 2008-500719 A | 1/2008 |
| WO | 2006/043329 A1 | 4/2006 |
| WO | 2007/083362 A1 | 7/2007 |

* cited by examiner

*Primary Examiner* — Kyoung Lee
(74) *Attorney, Agent, or Firm* — Canon USA Inc IP Division

(57) ABSTRACT

The present invention relates to a method of manufacturing a semiconductor device by which the length of nanowires perpendicularly formed can be fabricated with high reproducibility. The method of manufacturing a semiconductor device includes the steps of forming a first layer; forming a stop layer on the first layer, the stop layer having a higher Young's modulus than the first layer; forming a recess by partially removing the first layer and the stop layer; growing nanowires in the recess; forming a planarizing layer; removing the planarizing layer to the level of the stop layer to expose the nanowires from the surface of the planarizing layer; and forming an electrode so as to be in contact with the upper ends of the nanowires.

7 Claims, 5 Drawing Sheets

METHOD OF MANUFACTURING SEMICONDUCTOR DEVICE

TECHNICAL FIELD

The present invention relates to a method of manufacturing a semiconductor device having nanowires.

BACKGROUND ART

Along with the advancement of semiconductor processing technology, it has become difficult to achieve desired characteristics by means of the known two-dimensional scaling method. Furthermore, along with reduction in feature size, problems regarding the short-channel effects and the like have begun surfacing. Therefore, there has been a need for a breakthrough other than a simple reduction in feature size.

Semiconductor nanowires have been receiving attention because of the possibility of obtaining transistors having a good electrical characteristic, and the like. Examples of nanowire fabrication techniques include a top-down method in which lithography and etching are used and a bottom-up method typified by a vapor-liquid-solid (VLS) method. By using the bottom-up method, for example, it is possible to obtain nanowires composed of a single-crystal semiconductor which have a circular cross section with a diameter of 500 nm or less and which have a low crystal defect density. However, this method has not been put into practical use because of difficulties in control of growth orientation and position.

There is a known method in which grown nanowires are separated from a substrate by a stimulus, such as ultrasonic waves, in a solution, collected, and then applied and arranged horizontally on another substrate, followed by formation of electrodes on both ends. In this method, nanowires are laid out randomly on the surface of the substrate, and therefore, it is difficult to fabricate a device with high reproducibility of characteristics. Furthermore, since a complex process is required, mass production is difficult.

In contrast, PTL 1 discloses a method in which nanowires VLS-grown perpendicular to a substrate are, without using a step of relocation to another substrate, directly fabricated into a device on the substrate on which the nanowires have been grown.

CITATION LIST

Patent Literature

PTL 1 PCT Japanese Translation Patent Publication No. 2008-500719

SUMMARY OF INVENTION

Although the method described above has an advantage that a relocation process of nanowires is not required, the length of nanowires in the longitudinal axis direction after processing becomes unstable because of a process variation.

In particular, in the transistor application, a variation in the length of nanowires greatly influences the major characteristics, such as the drain current and the gate threshold voltage. More particularly, in the device fabrication method described in PTL 1, the length of electrodes, which corresponds to the gate length, is determined by forming a protection layer after formation of the individual electrodes and removing the excess portions. Consequently, the resulting gate length varies depending on the variation in the thickness of the protection layer and the variation in the electrode removing rate, and it is difficult to obtain sufficient reproducibility.

Furthermore, the distances among the source electrode, the drain electrode, and the gate electrode are determined by the thickness of a separation layer for electrical separation and the like. However, the thickness varies depending on the film deposition apparatus and the film deposition conditions. The variations cause a variation in parasitic capacitance between the adjacent electrodes, which can be a factor that causes a variation in the time constant in the device operation.

As described above, when nanowires are used in a vertical-type device, variations in film deposition in the direction perpendicular to a substrate and in processing greatly affect the device performance.

The present invention provides a method of manufacturing a device having nanowires with higher reproducibility.

According to the gist of the present invention, a method of manufacturing a semiconductor device includes the steps of forming a first layer on a substrate; forming a stop layer on the first layer, the stop layer having a higher Young's modulus than the first layer; forming a recess by partially removing the first layer and the stop layer such that a portion of the substrate is exposed; growing nanowires extending in a direction perpendicular to a surface of the substrate in the recess such that the length of the nanowires is larger than the sum of the thickness of the first layer and the thickness of the stop layer; forming a planarizing layer in the recess in which the nanowires have been grown, the planarizing layer having a thickness larger than the sum of the thickness of the first layer and the thickness of the stop layer and having a lower Young's modulus than the stop layer; removing the planarizing layer to the level of the stop layer to expose the nanowires from the surface of the planarizing layer; and forming an electrode so as to be in contact with the upper ends of the nanowires.

DESCRIPTION OF EMBODIMENTS

First Embodiment

Figure 1A:
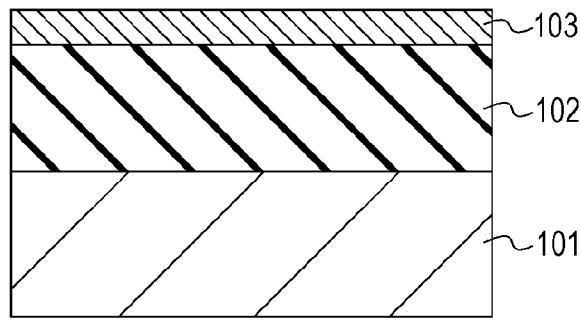
FIGS. 1A to 1G are schematic cross-sectional views showing the process steps of manufacturing a semiconductor device according to an embodiment of the present invention.

A method of manufacturing a semiconductor device according to an embodiment of the present invention will be described with reference to FIGS. 1A to 1G. Reference numeral 101 represents a substrate, reference numeral 102 represents a first layer, reference numeral 103 represents a stop layer, reference numeral 104 represents a recess, reference numeral 105 represents a catalyst, reference numeral 106 represents a semiconductor source material, reference numeral 107 represents a nanowire, reference numeral 108 represents a planarizing layer, reference numeral 109 represents an electrode, reference numeral 110 represents an insulating layer, and reference numeral 111 represents a conductive substance.

As shown in FIG. 1A, a thickness adjustment layer 102 as a first layer is formed on a substrate 101. As the material constituting the surface of the substrate 101 used in the present invention, a semiconductor material that can control the nanowire growth orientation during formation of nanowires using plane orientation dependence of surface potential may be used. Specifically, a semiconductor, such as Si, Ge, C, SiGe, or SiC, is used. Furthermore, in the case where a substrate or a surface layer region of a substrate is used as an electrode for nanowires, an impurity serving as an acceptor or a donor may be added to enhance conductivity. Specifically, using a Si substrate, a p-type impurity, such as boron, or an n-type impurity, such as phosphorus or arsenic, may be incorporated, at a density of $1 \times 10^{17}$ atoms/cm$^3$ or more, into at least a region in contact with the nanowires. This can be easily achieved by a combination of a lithography process with a process, such as ion implantation or impurity diffusion.

As the thickness adjustment layer 102 which is the first layer used in the present invention, a layer that can define the length of the nanowires may be used. The thickness of the thickness adjustment layer 102 is appropriately selected according to the required length of the nanowires. As the material for the thickness adjustment layer, an insulating layer can be used. Specifically, at least one inorganic insulator selected from silicon oxide, silicon nitride, silicon oxynitride, aluminum oxide, tantalum oxide, and the like may be used, and as necessary, the inorganic insulator may be doped with hydrogen, fluorine, carbon, or the like. Furthermore, the insulating layer serving as the thickness adjustment layer 102 may be composed of an organic insulator. Specific examples thereof include hydrogen silsesquioxane (HSQ), methyl-silsesquioxane (MSQ), BCB, and the like. Furthermore, the insulating layer serving as the thickness adjustment layer 102 is preferably composed of a material having a lower dielectric constant than silicon dioxide, and more preferably composed of a low dielectric constant insulating material with a relative dielectric constant of 3.0 or less from the standpoint of reduction in parasitic capacitance in the device operation. Specific examples thereof include HSQ, MSQ, SiOF, and the like. A porous film may be used instead of such materials or in combination with such materials. The insulating layer serving as the thickness adjustment layer 102 used in the present invention has a Young's modulus of preferably less than 100 GPa, more preferably less than 50 GPa, and still more preferably 10 Gpa or less. The thickness of the thickness adjustment layer is preferably 200 nm to 10 µm, and more preferably 500 nm to 5 µm. These layers can be formed by a known method, such as CVD, sputtering, or spin coating.

A stop layer 103 is formed on the thickness adjustment layer 102. The stop layer 103 used in the present invention is desirably composed of a film having excellent etching resistance or polishing resistance with respect to the planarizing layer, which will be described later, i.e., a material that can have a high etch selectivity or polish selectivity with respect to the planarizing layer. Furthermore, the stop layer 103 preferably has higher mechanical strength than the thickness adjustment layer 102. Therefore, the stop layer desirably has a higher Young's modulus than the thickness adjustment layer. Within the range satisfying the conditions described above, specifically, the stop layer 103 has a Young's modulus of preferably 100 GPa or more, and more preferably 200 GPa.

As the material for the stop layer used in the present invention, specifically, a nitride, such as dense silicon nitride having a N/Si stoichiometric ratio of about 1.33, or an oxide, such as aluminum oxide or zirconium oxide, can be used. Other examples of the material for the stop layer include an inorganic substance, such as diamond or diamond-like carbon; a carbide typified by SiC; and a phosphate compound typified by hydroxyapatite. The layers composed of these materials can have a Young's modulus of 200 GPa or more, and can be formed by CVD, ALD, sputtering, or the like.

In view of the fact that Young's modulus is an indicator for strain with respect to stress, in an electrode and an insulating layer which is provided on and/or under the electrode and which electrically insulates the electrode from its adjacent electrode, the Young's modulus of the electrode is preferably close to that of the insulating layer. Preferably, the Young's modulus of the insulating layer is one fifth to five times that of the electrode. Ti, Cu, and W as the typical materials for the electrode have a Young's modulus of about 100 to 400 GPa. It is preferable to use, as the stop layer, an insulating layer having a Young's modulus close to that of these materials in view of prevention of film peeling off.

The stop layer is preferably thinner than the thickness adjustment layer 102, and the thickness of the stop layer is preferably 10 nm or more and less than 200 nm, and more preferably 50 nm or more and less than 200 nm. A film with high mechanical strength often has a low film formation rate, and it is expected that, by forming a thick film, the process cost and the load on machine time will increase. In addition, stress in the film is large, and there is a possibility of occurrence of cracks, peeling off from the substrate, and the like resulting from formation of a thick film. Thus, there are many constraints in increasing the thickness of the film.

Figure 1B:
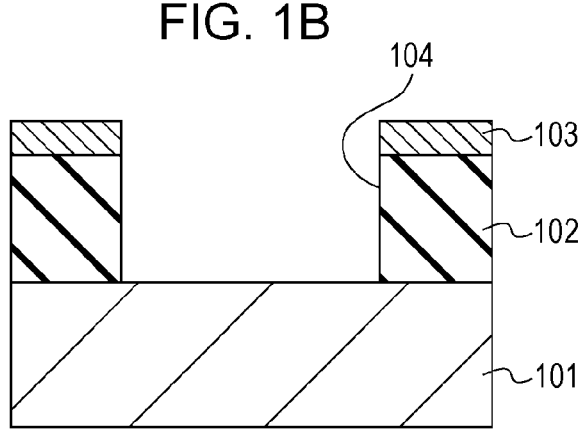

Next, as shown in FIG. 1B, after the formation of the stop layer 103, the stop layer 103 and the thickness adjustment layer 102 are partially removed until the surface of the substrate 101 is exposed, thereby to form a recess 104. Removal of the stop layer 103 and the thickness adjustment layer 102 for forming the recess 104 can be performed by wet etching, dry etching, or the like.

Figure 1C:
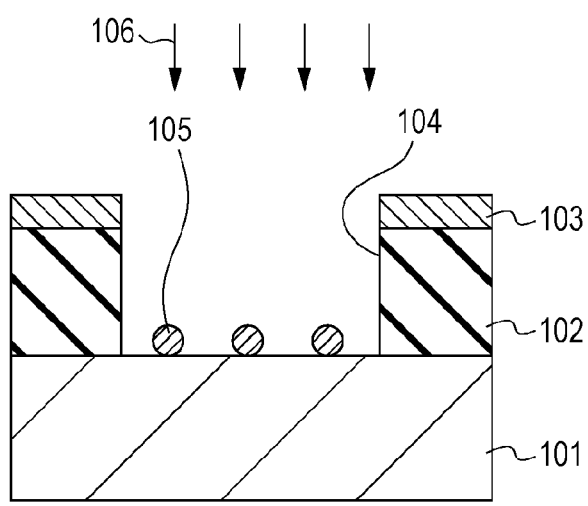

As shown in FIG. 1C, a catalyst 105 is deposited on the exposed portion where the substrate is exposed in the recess 104. As the catalyst 105 used in the present invention, at least one material which is selected from Au, Al, Si, Sn, Pb, Ni, Fe, Ag, and the like and which forms a eutectic with a semiconductor, such as Si, Ge, or C, for forming nanowires, which will be described later, can be used.

The catalyst 105 can be deposited by a lift-off process or by patterning using ordinary lithography. Furthermore, the catalyst 105 can also be deposited by dropwise addition of a solution containing metal fine particles (e.g., a Au colloid-containing solution or a Ag colloid-containing solution) onto the substrate. In the case where the catalyst melts to droplets, the particle diameter is preferably 200 nm or less. The reason for this is that supersaturation in VLS growth of nanowires, which will be described later, can take place more appropriately. In the case where a thin-film catalyst is used, the particle diameter can be controlled by the initial film thickness and annealing conditions before supplying a semiconductor source material for forming nanowires. For example, in the case where a Au thin film with a thickness of 3 nm is used, by heating for about two to five minutes at 370° C. in an inert gas, such as nitrogen or argon, with a partial pressure of 133 Pa in a vacuum chamber, it is possible to form catalyst particles with a particle diameter of about 40 nm in a dispersed manner for obtaining nanowires. In the meantime, in the case where a colloid is used, nanowires having a diameter substantially the same as the diameter of initial colloidal particles can be obtained.

Next, a nanowire source material 106 that can form a eutectic with the catalyst 105 is supplied, and the substrate 101 is heated to a temperature at which the catalyst and the semiconductor for nanowires can form a eutectic state. For example, in silicon nanowire growth using a Au catalyst, the temperature is set higher than the eutectic temperature of 363° C.

As the semiconductor source material 106, a gas containing atoms constituting nanowires, such as $SiH_4$, $SiF_4$, $SiCl_4$, $SiHCl_3$, $SiH_2Cl_2$, $GeH_4$, $CH_4$, or $C_2H_6$, can be used. Furthermore, using a technique, such as PLD or sputtering, supply can be performed in the vapor phase from a solid semiconductor source material which is a vapor deposition source or a target. By supplying the semiconductor source material 106, the semiconductor species melts into the catalyst 105 to form molten droplets in a eutectic state. By continuing to supply the semiconductor source material 106, the semiconductor species reaches supersaturation in the molten droplets, which leads to semiconductor crystal growth. This is the VLS growth method, and nanowires are obtained by this method. For example, by using $SiH_4$ gas as the semiconductor source material 106, silicon nanowires are obtained, and by using $GeH_4$, germanium nanowires are obtained. Besides the VLS method, a vapor-solid-solid (VSS) method or an MOCVD method can be used depending on the material. By using these methods, nanowires extending in a direction perpendicular to the surface of the substrate can be grown.

The nanowires used in the present invention have a diameter of preferably 1 to 200 nm, and more preferably 5 to 100 nm. Preferably, the nanowires contain at least one semiconductor selected from the group consisting of group IV element semiconductors, III-V compound semiconductors, and II-VI compound semiconductors in the amount of 90% by weight or more.

The group IV element is preferably Si, Ge, or C. In the III-V compound, preferably, the group III element is one or a combination of two or more of Ga, Al, and In, and the group V element is N, P, As, Sb, or Bi. In the II-VI compound, preferably, the group II element is Zn or Cd, and the group VI element is O, Se, or Te.

Figure 1D:
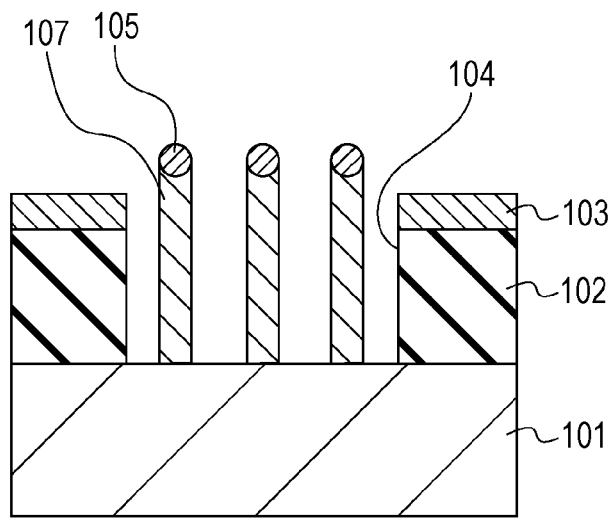

In this process step, as shown in FIG. 1D, nanowires 107 are formed such that the length of the nanowires 107 is larger than the total (sum) of the thickness of the thickness adjustment layer 102 and the thickness of the stop layer 103. In the case where chemical vapor deposition (CVD), which is widely used in semiconductor processes, is used, the film thickness is controlled by the deposition rate and the deposition time. The reason for this is that, by etching and/or polishing to the level of the stop layer in the back-end process, the nanowires are exposed.

Figure 1E:
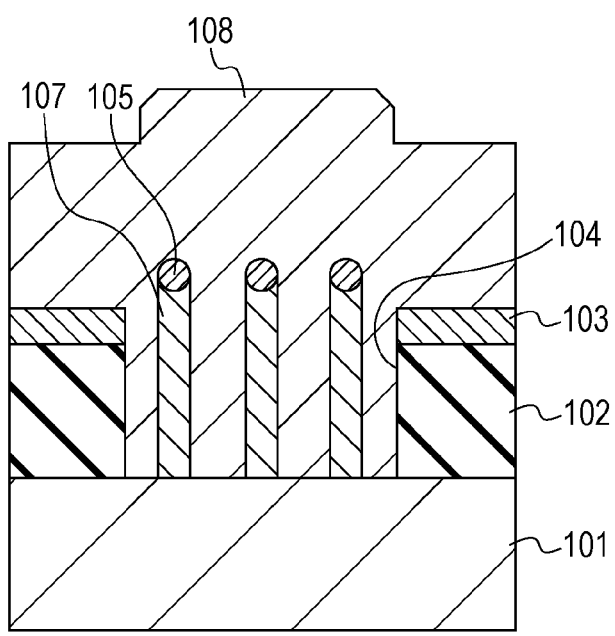

Subsequently, as shown in FIG. 1E, a planarizing layer 108 is formed, the planarizing layer 108 having a thickness sufficiently larger than the total (sum) of the thickness of the thickness adjustment layer 102 and the thickness of the stop layer 103. The planarizing layer 108 used in the present invention preferably has lower mechanical strength than the stop layer 103, and sufficient ability of covering the step of the recess 104 and the nanowires 107. The planarizing layer 108 has a lower Young's modulus than the stop layer 103. Specifically, the Young's modulus of the planarizing layer 108 is preferably less than 100 GPa, and more preferably 50 GPa or less. As the planarizing layer, an insulating organic polymer can be used. For example, PMMA can be used, and the planarizing layer can be formed by spin coating. In the case where the recess 104 has a width of 10 μm or less, in order to facilitate burying the recess, more preferably, dilution is performed with an organic solvent, such as methyl isobutyl ketone or ethylene glycol monoethyl ether acetate. Furthermore, after application of PMMA, baking is preferably performed at about 120° C. for about 2 min. The organic solvent contained in PMMA is evaporated by the baking, which increases the hardness of PMMA, resulting in improvement in durability and stability in the washing step, the polishing step, and the like of the back-end process. Even after baking, the Young's modulus of PMMA or the like is 50 GPa or less. The planarizing layer makes it possible to obtain a smooth polished surface and also has a function of preventing nanowires from being damaged, falling, or the like in the polishing step of the back-end process.

Figure 1F:
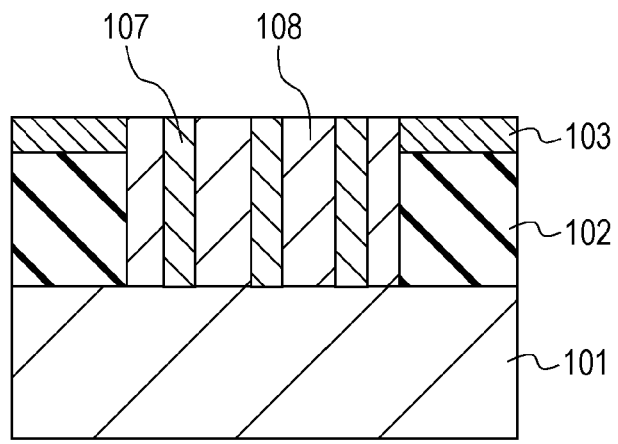

Subsequently, as shown in FIG. 1F, the planarizing layer 108 is removed to the upper surface of the stop layer 103. As the removal method, etching and/or chemical mechanical polishing is suitably used. Here, chemical mechanical polishing can be used. When the removal by polishing reaches the stop layer, the removing rate rapidly decreases because the mechanical strength of the stop layer is larger than that of the planarizing layer. By stopping the removal process during the period from when the surface exposed by removal by polishing reaches the upper surface of the stop layer until the surface exposed reaches the lower surface of the stop layer, the removal ceases within the stop layer. The nanowires 107 are formed such that the length of the nanowires 107 is larger than the total (sum) of the thickness of the thickness adjustment layer 102 and the thickness of the stop layer 103. Consequently, the nanowires 107 are removed to the length close to the total thickness of the thickness adjustment layer 102 and the stop layer 103, and after the removal, the ends of the nanowires are exposed from the planarizing layer. In FIG. 1F, the surfaces of the ends of the nanowires and the surface of the planarizing layer 108 are aligned at the same level. However, the ends of the nanowires may slightly protrude because of the difference in the polishing rate. In such a manner, the stop layer functions as an etching stopper or a polishing stopper.

In the case where etching is used for removing the planarizing layer, the entire surface of the planarizing layer is etched back using an etchant having substantially the same etching rate for the constituent material for the nanowires and the constituent material for the planarizing layer and an etching rate lower for the stop layer.

Figure 1G:
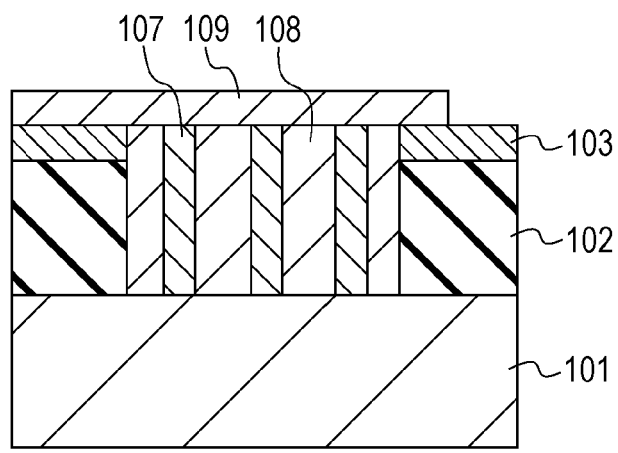

Subsequently, as shown in FIG. 1G, an electrode 109 is formed so as to be connected to the exposed upper ends of the nanowires 107. The electrode is partially formed such that at least a portion of the stop layer 103 is exposed.

The material for the electrode may be a metal or a high impurity concentration semiconductor containing carriers in an amount sufficient to allow nanowires to operate for a device. For example, polycrystalline silicon which is formed by sputtering or CVD and doped with an impurity in the back-end process can be used.

In the case of a metal, a metal having a work function suitable for the Fermi level of the semiconductor constituting the nanowires according to the device design can be used. Furthermore, in the case of a semiconductor, it is possible to obtain a contact according to the device design by forming a film having a suitable Fermi level by selecting an appropriate dopant gas species and concentration level.

The electrode can be a metal, a semiconductor doped with an impurity, or a silicide. Examples of the metal include an elemental metal or an alloy containing at least one selected from the group consisting of Ta, Ni, Ti, Al, Au, Pt, Mo, Cr, W, Cu, Ag, and the like.

Specific examples of the semiconductor include at least one selected from Si, Ge, and C, and examples of the impurity include at least one selected from B, P, and As. Examples of the silicide include silicon compounds containing Si and at least one selected from Ti, Zr, Hf, V, Nb, Ta, Cr, W, Mn, Tc, Re, Fe, Ru, Os, Co, Rh, Ir, Ni, Pd, Pt, Al, and the like.

In the case where a two-terminal device is fabricated as a semiconductor device having nanowires, a structure shown in FIG. 1G can be employed.

Second Embodiment

The case where a three-terminal device is fabricated will now be described with reference to FIGS. 2A to 2C.

Figure 2A:
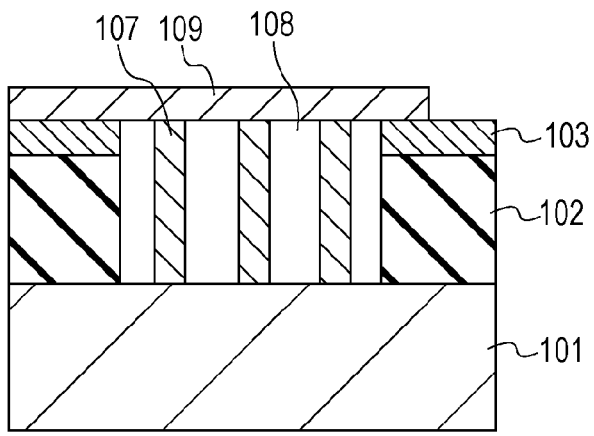
FIGS. 2A to 2C are schematic cross-sectional views showing the process steps of manufacturing a semiconductor device according to another embodiment of the present invention.

After the structure shown in FIG. 1G is obtained, as shown in FIG. 2A, the planarizing layer 108 is removed. The structure is immersed in a solution that can selectively dissolve the planarizing layer 108 such that the surface of the recess 104 embedded in the planarizing layer 108 is exposed. Thereby, the planarizing layer 108 inside the recess 104 is removed. For example, when PMMA is used as the planarizing layer, acetone can be used.

Figure 3:
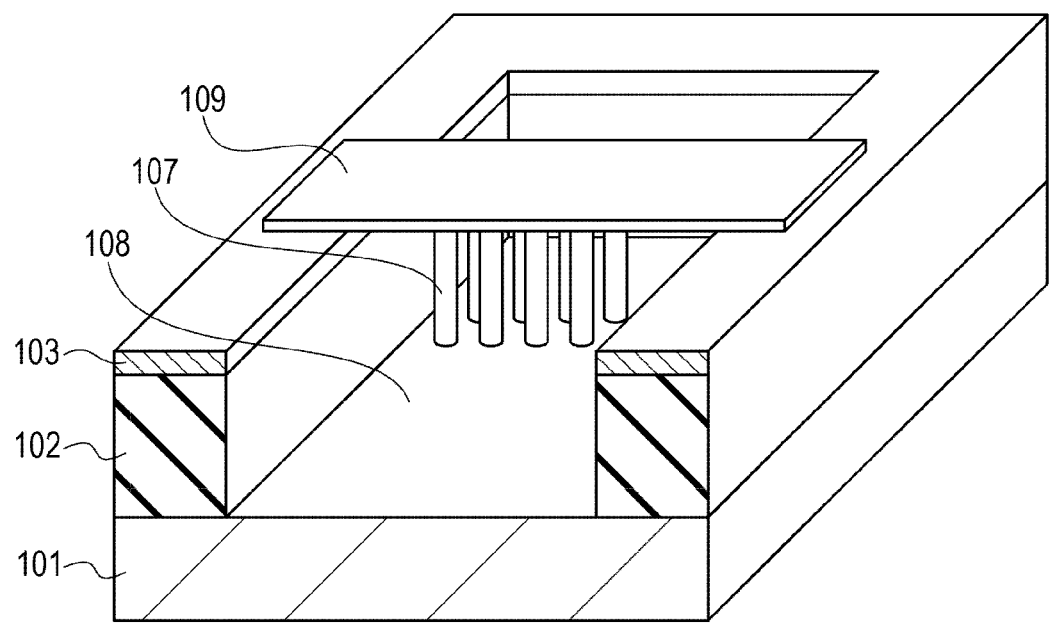
FIG. 3 is a schematic perspective view of a semiconductor device according to another embodiment of the present invention.

Incidentally, in the case of a two-terminal device, a state shown in FIG. 3 may be used.

Figure 2B:
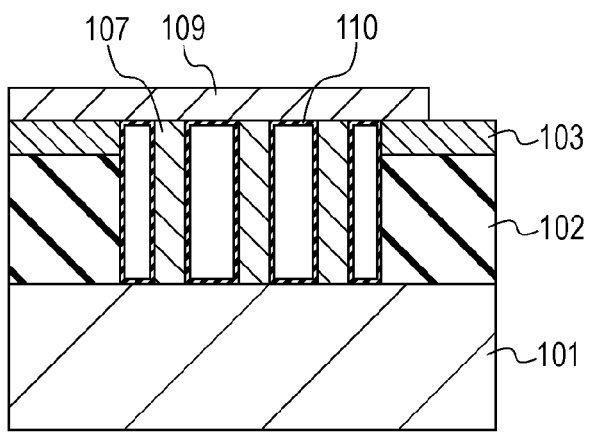

Next, as shown in FIG. 2B, an insulating layer 110 is formed so as to cover the surfaces of the nanowires 107, the substrate 101, the electrode 109, the thickness adjustment layer 102, and the stop layer 103 which have been exposed at the recess 104 by the removal of the planarizing layer 108. In this process step, a film formation method and a material can be selected appropriately depending on the materials for the nanowires and the electrode. For example, in the case where the nanowires are composed of silicon and the electrode is composed of a metal, such as Ti or W, a vapor-phase growth method, such as low-pressure (LP) CVD or atomic layer deposition (ALD), is suitably used. In the case where the nanowires and the electrode are each composed of silicon, an oxide film as the insulating layer 110 may be formed by surface modification, such as immersion into aqueous hydrogen peroxide or thermal oxidation.

Figure 2C:
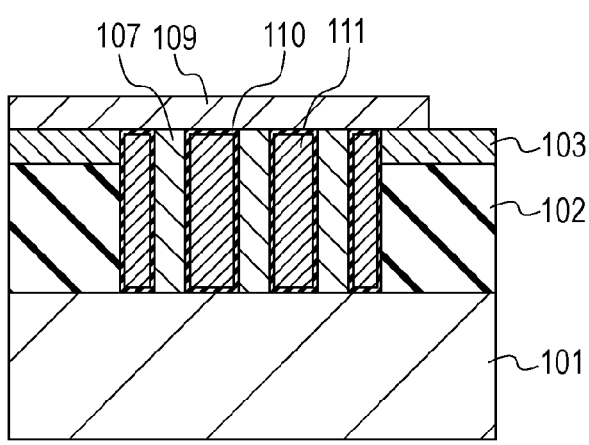

Subsequently, as shown in FIG. 2C, a conductive substance 111 is disposed in the recess 104. In the case where the conductive substance 111 is a metal, the conductive substance can be deposited, for example, by CVD or sputtering and an annealing step for reflowing in combination therewith. In this case, as necessary, an electrode for applying a potential to the conductive substance 111 is formed at a position (not shown) that is not electrically connected to the electrode 109 in an opening of the recess 104 not covered with the electrode 109. In such a manner, a potential can be applied to the conductive substance 111 from the outside. The electrode (not shown) can be formed by a known film formation method and patterning.

Furthermore, as the conductive substance 111, a conductive polymer can also be used, which is easier to form. Furthermore, the conductive substance 111 can also be formed by filling the recess with an electrolytic solution. In this case, a potential can be applied to the conductive substance 111 composed of an electrolyte by inserting an electrode composed of a conductor into the conductive substance 111 at a position not electrically connected to the electrode 109.

In the structure described above, the conductive substance 111 is disposed at substantially the same distance from the upper surface of the substrate 101, the side surfaces of the thickness adjustment layer 102 and the stop layer 103, the side surfaces of the nanowires 107, and the lower surface of the electrode 109 with the insulating layer 110 therebetween. When a voltage is applied to the conductive substance 111, potential variations are induced in the substrate 101, the nanowire 107, and the electrode 109. A potential is applied between the substrate 101 and the electrode 109, and a potential is applied to the conductive substance 111. When such potentials are applied, a potential variation at the nanowires 107 which have the smallest cross-sectional area as the conductive path for carriers and the resulting change in the carrier accumulation state cause the largest change in the current flowing between the substrate 101 and the electrode 109. Thus, the three-terminal device shown in FIG. 2C functions as a field-effect transistor. In this case, the conductive substance serves as a gate electrode. One of the substrate 101 and the electrode 109 serves as a source electrode, and the other serves as a drain electrode.

In the case where the substrate 101 contains a large amount of an n-type impurity, carriers controlled by the operation of the transistor are electrons, and an re-channel transistor is produced. Consequently, one of the substrate 101 and the electrode 109 which has a relatively positive potential serves as a drain electrode, and the other which has a relatively negative potential serves as a source electrode. Conversely, in the case where the substrate 101 contains a large amount of a p-type impurity, carriers controlled by the operation of the transistor are holes. One of the substrate 101 and the electrode 109 which has a relatively positive potential serves as a source electrode, and the other which has a relatively negative potential serves as a drain electrode.

Third Embodiment

A case where a semiconductor device of the present invention is used as a sensor will now be described.

The case where the potential of the conductive substance varies in the state in which a certain amount of voltage is applied between the source and the drain corresponds to a case where the voltage applied to the gate in the transistor varies, and therefore, the drain current characteristic in the transistor changes. Using this phenomenon, it is possible to use the semiconductor device as a sensor that detects a variation in the potential of the conductive substance. For example, in the case where the conductive substance 111 is an electrolytic solution having a certain pH, when the pH varies, the electrochemical potential varies according to the Nernst equation, and therefore, the drain current changes. In such a manner, the semiconductor device can be used, for example, as a pH sensor.

Fourth Embodiment

A case where a semiconductor device of the present invention is used as a sensor will now be described.

When a material that specifically reacts with a target molecule and varies the potential in the nanowires by the interaction is immobilized onto the surface of the insulating layer 110 covering the nanowires 107, a semiconductor device functioning as a molecular sensor is produced. Such a material can be a biomolecule, such as an antigen, an antibody, or an oligonucleotide.

Specifically, a semiconductor device is fabricated by the method described above up to the process step before deposition of the conductive substance 111. Then, the exposed surface of the recess is terminated with amino groups by immersion in a silane coupling agent, and by introducing thereto a first oligonucleotide which has a specific sequence and a molecular end of which is modified with a carbonyl group, the first oligonucleotide is immobilized onto the recess. Next, when an electrolytic solution containing a second oligonucleotide having a sequence complementary to that of the first oligonucleotide is introduced to the recess, only the second oligonucleotide having the complementary structure forms a complementary strand with the first oligonucleotide on the surface of the recess and is captured. Since each pair of phosphate groups in an oligonucleotide has a negative charge, positive charges are induced in the nanowires by immobilization of the first oligonucleotide at the surface portion of the insulating layer 110 covering the nanowires 107. In addition, when a second oligonucleotide that forms a complementary strand with the first oligonucleotide is introduced to the recess, charges owned by the second oligonucleotide further electrostatically induce charges in the nanowires in the vicinity of the surface. At this time, if a certain voltage is applied between the source and the drain, the number of carriers flowing into the drain varies. The amount of variation in current between the source and the drain after the first oligonucleotide has been immobilized changes depending on the amount of the second oligonucleotide that forms a complementary strand with the first oligonucleotide immobilized onto the surface portion of the nanowires 107. As a result, the semiconductor device functions as a molecule-recognition sensor that can selectively and quantitatively detect the second oligonucleotide.

As described above with reference to the embodiments and examples, according to the present invention, after growing nanowires having a length larger than the sum of the thickness of a first layer and a stop layer, a planarizing layer is formed so as to extend over the upper surface of the stop layer. Then, the planarizing layer can be removed. Since the removing rate of the planarizing layer rapidly decreases at the stop layer, the upper surface of the stop layer and the upper ends of the nanowires are aligned, and the height, namely, the length, of the nanowires is determined in a self-aligned manner. Thus, it is possible to manufacture a semiconductor device having nanowires with a desired length with high reproducibility.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-054718 filed Mar. 11, 2010, which is hereby incorporated by reference herein in its entirety.

The invention claimed is:

1. A method of manufacturing a semiconductor device comprising the steps of:
    forming a first layer on a substrate;
    forming a stop layer on the first layer, the stop layer having a higher Young's modulus than the first layer;
    forming a recess by partially removing the first layer and the stop layer such that a portion of the substrate is exposed;
    growing nanowires extending in a direction perpendicular to a surface of the substrate in the recess such that the length of the nanowires is larger than the sum of the thickness of the first layer and the thickness of the stop layer;
    forming a planarizing layer in the recess in which the nanowires have been grown, the planarizing layer having a thickness larger than the sum of the thickness of the first layer and the thickness of the stop layer and having a lower Young's modulus than the stop layer;
    removing the planarizing layer to the level of the stop layer to expose the nanowires from the surface of the planarizing layer; and
    forming an electrode so as to be in contact with the upper ends of the nanowires.

2. The method of manufacturing a semiconductor device according to claim 1, further comprising the steps of:
    forming an insulating layer so as to cover the nanowires, the substrate, and the electrode which have been exposed at the recess; and
    disposing a conductive substance in the recess provided with the insulating layer.

3. The method of manufacturing a semiconductor device according to claim 1, wherein, in the step of growing nanowires, a catalyst is deposited on the exposed portion of the substrate, and by supplying a gas containing atoms of a semiconductor that can form a eutectic with the catalyst, the nanowires composed of the semiconductor are grown.

4. The method of manufacturing a semiconductor device according to claim 1, wherein the stop layer has a Young's modulus of 200 GPa or more.

5. The method of manufacturing a semiconductor device according to claim 1, wherein the first layer is an insulating layer having a thickness larger than that of the stop layer and a Young's modulus of less than 100 GPa.

6. The method of manufacturing a semiconductor device according to claim 1, wherein the step of removing the planarizing layer is carried out by chemical mechanical polishing.

7. The method of manufacturing a semiconductor device according to claim 1, further comprising the steps of:
    forming an insulating layer so as to cover the nanowires, the substrate, and the electrode which have been exposed at the recess; and
    disposing a material that specifically reacts with a target molecule on the insulating layer.

* * * * *